United States Patent
Charles et al.

(10) Patent No.: US 11,538,585 B2
(45) Date of Patent: Dec. 27, 2022

(54) DETECTING ABNORMALITIES IN ECG SIGNALS

(71) Applicant: Cambridge Heartwear Limited, Cambridge (GB)

(72) Inventors: James Charles, Cambridge (GB); Rameen Shakur, Cambridge (GB); Roberto Cipolla, Cambridge (GB)

(73) Assignee: Cambridge Heartwear Limited, Cambridge (GB)

( * ) Notice: Subject to any disclaimer, the term of this patent is extended or adjusted under 35 U.S.C. 154(b) by 1135 days.

(21) Appl. No.: 16/003,897

(22) Filed: Jun. 8, 2018

(65) Prior Publication Data

US 2019/0378617 A1    Dec. 12, 2019

(51) Int. Cl.
| | |
|---|---|
| *A61B 5/00* | (2006.01) |
| *G16H 50/20* | (2018.01) |
| *G16H 40/63* | (2018.01) |
| *G06N 3/04* | (2006.01) |
| *G06N 3/08* | (2006.01) |
| *A61B 5/316* | (2021.01) |

(Continued)

(52) U.S. Cl.
CPC ........... *G16H 50/20* (2018.01); *A61B 5/0006* (2013.01); *A61B 5/316* (2021.01); *A61B 5/332* (2021.01); *A61B 5/361* (2021.01); *A61B 5/7203* (2013.01); *G06N 3/04* (2013.01); *G06N 3/08* (2013.01); *G16H 40/63* (2018.01)

(58) Field of Classification Search
CPC ....... A61B 5/0006; A61B 5/316; A61B 5/332; A61B 5/361; A61B 5/7203; A61B 5/7267; G06N 3/04; G06N 3/0454; G06N 3/0481; G06N 3/08; G16H 40/63; G16H 50/20; G16H 50/70
See application file for complete search history.

(56) References Cited

U.S. PATENT DOCUMENTS

| | | | |
|---|---|---|---|
| 6,658,287 B1 * | 12/2003 | Litt | G16H 50/20 600/544 |
| 10,602,942 B2 | 3/2020 | Shakur et al. | |
| 11,013,470 B2 | 5/2021 | Shakur et al. | |

OTHER PUBLICATIONS

NHS, "Arrhythmia", Jul. 8, 2015, London, UK, downloaded Sep. 6, 2018, http://www.nhs.uk/conditions/arrhythmia/Pages/arrhythmia.aspx.

(Continued)

*Primary Examiner* — George Manuel
(74) *Attorney, Agent, or Firm* — Hamilton, Brook, Smith & Reynolds, P.C.

(57) ABSTRACT

A method of detecting abnormalities in ECG signals by providing an ECG signal to a neural network, performing a first series of convolution operations to a first subset of layers and in a final layer, and determining a plurality of preliminary classification estimates, each preliminary classification estimate corresponding with a time segment of the ECG signal. Furthermore, determining input data for a second subset of layers of the neural network by concatenating the preliminary classification with the output of a layer of the first subset of layers that precedes the final layer of the first subset of layers. Within the second subset of layers of the neural network, performing a second series of convolution operations. In a final layer of the second subset, determining plurality of final classification estimates, each final classification estimate corresponding with a time segment of the ECG signal.

20 Claims, 6 Drawing Sheets

(51) Int. Cl.
A61B 5/332 (2021.01)
A61B 5/361 (2021.01)

(56) References Cited

OTHER PUBLICATIONS

Atrial Fibrillation Assoc., Warwickshire, Anticoagulation Europe; "The AF report. Atrial fibrillation—preventing a stroke crisis", Kent, UK, Apr. 12, 2012, http://www.preventaf-strokecrisis.org/files/files/The AF Report Apr. 14, 2012.pdf.
K. Carroll, S. Murad, J. Eliahoo, A. Majeed, "Stroke incidence and risk factors in a population-based prospective cohort study," Office for National Statistics, Newport, South Wales, UK, Rep. Health Statistics Quarterly 12, 2001. http://www.ons.gov.uk/ons/rel/hsq/health-statistics-quarterly/no—12—winter-2001/stroke-incidence-and-risk-factors-in-a-population-based-prospective-cohort-study.pdf.
C. Marini et al., abstract of "Contribution of atrial fibrillation to incidence and outcome of ischemic stroke: results from a population-based study," Stroke, vol. 36, pp. 1115-1119, May 5, 2005.
D. M. Lloyd-Jones et al., abstract of "Lifetime risk for development of atrial fibrillation: the Framingham heart study," Circulation, vol. 110, No. 9, pp. 1042-1046, Aug. 31, 2004.
G. Y. H. Lip and H. S. Lim, abstract of "Atrial fibrillation and stroke prevention," The Lancet Neurology, vol. 6, No. 11, pp. 981-993, Nov. 2007.
M. Cesarelli, P. Bifulco, and M. Bracale, "An algorithm for the detection of the atrial fibrillation from the surface ECG for an of home-care evaluation of the implanted atrial defibrillators," in Proc. Mediterranean Conf. Medical and Biological Eng. and Computing, Cyprus, 1998, 5 pgs.
M. Carrara et al., abstract of "Classification of cardiac rhythm using heart rate dynamical measures: validation in MIT-BIH databases," J. of Electrocardiology, vol. 48, No. 6, pp. 943-946, Nov.-Dec. 2015.
J. S. Healy et al., "Subclinical atrial fibrillation and the risk of stroke," The New England J. of Medicine, vol. 366, No. 2, pp. 120-129, Jan. 12, 2012.
Melo, SL, Caloba, LP, and Nadal, J. Arrhythmia analysis using artificial neural network and decimated electrocardiographic data, Computers in Cardiology 2000, pp. 73-76.
Moody, George B and Mark, Roger G. "A new method for detecting atrial fibrillation using RR intervals", Computers in Cardiology, 10(1):227-230, 1983.
Pan, Jiapu and Tompkins, Willis J. "A real-time QRS detection algorithm", IEEE transactions on biomedical engineering, (3):230-236, 1985.
Clifford, GD, Liu, CY, Moody, B, Lehman, L, Silva, I, Li, Q, Johnson, Aew, and Mark, RG. "AF classification from a short single lead ecg recording: The physionet/computing in cardiology challenge 2017", 2017.
Artis, Shane G, Mark, Rg, and Moody, GB. "Detection of atrial fibrillation using artificial neural networks". In Computers in Cardiology 1991, Proceedings., pp. 173-176. IEEE, 1991.
Levin Tan. Fourth year project technical report regarding Atrial Fibrillation, date unknown, 44 pgs.
Schwab, P., Scebba, G., Zhang, J., Delai, M. and Karlen, W. "Beat by Beat: Classifying Cardiac Arrhythmias with Recurrent Neural Networks", Mobile Health Systems Lab, Department of Health Sciences and Technology ETH Zurich, Switzerland, Oct. 24, 2017, 4 pgs.
Rajpurkar, P., Hannun, A.Y., Haghpanahi, M., Bourn, C. and Ng, A.Y. "Cardiologist-level arrhythmia detection with convolutional neural networks", Jul. 6, 2017, 9 pgs.
Pfister, T. and Charles, J. and Zisserman, A. "Flowing ConvNets for Human Pose Estimation in Videos, International Conference on Computer Vision", 2015, 9 pgs.
Yu, F. and Koltun, V. "Multi-scale context aggregation by dilated convolutions", Published as a conference paper at ICLR, Apr. 30, 2016, 13 pgs.
Abhilasha M. Patel et al., Real time ECG Feature Extraction and Arrhythmia Detection on a Mobile Platform, International Journal of Computer Applications (0975-8887), vol. 44—No. 23, Apr. 2012.
Shaojie Bai et al., Convolutional Sequence Modeling Revisited, Sixth International Conference on Learning Representations 2018, Workshop track—ICLR 2018.
Serkan Kiranyaz et al., Real-Time Patient-Specific ECG Classification by 1-D Convolutional Neural Networks, IEEE Transactions on Biomedical Engineering, vol. 63, No. 3, Mar. 2016.
Notification of Transmittal of The International Search Report and The Written Opinion of the International Searching Authority for PCT Application No. PCT/GB2019/051607 "Detecting Abnormalities in ECG Signals" dated Sep. 5, 2019.

* cited by examiner

DETECTING ABNORMALITIES IN ECG SIGNALS

FIELD OF THE INVENTION

The present disclosure relates to a method and apparatus for detecting abnormalities in electrocardiogram (ECG) signal, and to a system for improving cardiovascular health.

BACKGROUND TO THE INVENTION

Every year, more than 2 million people in the UK are affected by cardiac arrhythmia (heart rhythm abnormalities) which can lead to stroke, cardiac arrest, or even sudden cardiac death. In particular, atrial fibrillation (AF) is responsible for 20% of all strokes caused by clots (ischemic stroke). The population of AF patients is around 1.5 million in the UK alone.

However, early detection allows the commencement of treatment which can allow patients to lead a normal life, and thus is of great importance. Yet, AF in early stages occurs sporadically and inconsistently in short episodes, termed "paroxysmal AF", which may be difficult to detect in short tests. This is before developing into more sustained episodes, termed "persistent AF". In these early stages, round-the-clock monitoring is necessary to capture these short episodes.

Existing solutions are adequate in detecting what is known as "clinical AF", by operating on the order of minutes and diagnosing based on the fraction of time spent in AF and non-AF. This approach minimises the potential for false alarms. However, very short episodes of AF that may be "subclinical" during the paroxysmal stage may go undetected by such algorithms.

AF is the most common type of cardiac arrhythmia and is a condition of the heart whereby the atria (upper chambers of the heart) do not coordinate well to pump blood through the body. This may allow blood clots to form, which can lead to a stroke when they travel to the brain.

Having AF increases the risk of stroke in patients by 5 times, and the overall risk of death in patients by twice. A stroke afflicts 100,000 people per year in England and Wales (equivalent to one person every 5 minutes), and 20% of all strokes caused by such clots (known as an ischemic stroke) result from AF. An estimated 1.5 million people in the UK have AF currently, and the NHS spends over £2.2 billion a year on treating AF and AF related illnesses. By the time adults reach 40 years of age, they have a lifetime risk of about 25% of developing AF.

If AF is detected, patients may be put on treatment and medication like blood thinners (Warfarin in particular), which can reduce the risk of stroke by up to two thirds, and the risk of death by one third without significantly increasing the risk of major bleeding. Stroke patients require a long recovery, and many suffer permanent neural damage. This has a significant impact on the workforce and economy, estimated to be around £2.4 billion per annum.

FIG. 1 illustrates a basic electrocardiograph (ECG) signal. This has several points, which are labelled as P, Q, R, S, and T. These features arise from the electrical signals that pass through the different heart muscles in a procedural manner to allow the heart to pump blood normally. The voltage and time statistics (height, width, and time intervals of the various features) are key to diagnosing abnormalities in the heart rhythm. Most significantly, the P wave is the result from activity in the atria.

FIG. 2 illustrates a series of ECG signals which may be used for the detection of AF by doctors in clinics. They are, in order of reliability:

Irregularly irregular R-R intervals
Missing P waves
Presence of fibrillatory waves in the ECG base line.

Using each indicator on its own has its setbacks but these indicators work well when used together. Irregular R-R intervals, while being the easiest to detect in most circumstances, may not indicate AF in some cases, as there are various other arrhythmia that also exhibit irregular R-R intervals.

Missing P waves are difficult to observe in cases where there are high noise levels, which can obscure the baseline of the ECG signal, or if the ECG leads are not placed in positions to efficiently pick up electrical signals from the atria. There are also other arrhythmia that exhibit delayed, or advanced, P waves, complicating the detection.

Fibrillatory waves on the ECG base line are the hardest to observe because they are irregular and vary in amplitude from coarse to fine. Thus they are easily obscured by noise and other interference such as electrical activity from muscles. Owing to this, fibrillatory waves are considered a "soft marker" for AF.

To make matters worse, AF occurs sporadically (termed "paroxysmal AF") in a patient at an early stage, before becoming continuous (termed "persistent AF") in a later stage of the patient. While in the early stage, a patient may only exhibit AF under specific physiological conditions (e.g. when under physical stress, if they consume alcohol, etc) and these sporadic episodes of AF may occur for very short periods of time, on the order of seconds. This means that for early detection, round-the-clock monitoring is needed so that there is the opportunity to capture and recognise these short episodes of AF.

Computer algorithms already exist for the detection of AF. The usual approach is to diagnose AF by a threshold of AF burden (i.e. percentage of beats which are AF in a certain time window), as seen in M. Carrara et al., "Classification of cardiac rhythm using heart rate dynamical measures: validation in MIT-BIH databases," J. of Electrocardiology, vol. 48, no. 6, pp. 943-946, November-December 2015. DOI: 10.1016/j.jelectrocard.2015.08.002, to reduce false positives and diagnosis. This works well for the diagnosis of what is termed as "clinical AF".

However, during the stage of paroxysmal AF, such episodes can be short enough that they can be passed over by such detection algorithms. These very short episodes are termed "subclinical AF". According to a recent investigation J. S. Healy et al., "Subclinical atrial fibrillation and the risk of stroke," The New England J. of Medicine, vol. 366, no. 2, pp. 120-129, 12 Jan. 2012. DOI: 10.1056/NEJMoa1105575, being diagnosed with subclinical AF places an individual at 5.5 times the risk of developing clinical AF, and 2.5 times the risk of stroke, both within a period of approximately 2.5 years. Early detection of AF can thus have significant impact, but requires acute accuracy in the algorithm, and at high resolutions.

Machine learning techniques have been used to classify ECG data, such as applicants U.S. application Ser. No. 15/686,948, filed Aug. 25, 2017, "A Method of Detecting Abnormalities in ECG Signals" the contents of which are hereby incorporated by reference, but considerable room for improvement exists.

SUMMARY OF THE INVENTION

According to a first aspect, there is provided a method of detecting abnormalities in ECG signals, comprising:

providing an ECG signal to a neural network;

within a first subset of layers of the neural network, performing a first series of convolution operations;

in a final layer of the first subset of layers, determining a preliminary classification comprising a plurality of preliminary classification estimates, each preliminary classification estimate corresponding with a time segment of the ECG signal;

determining input data for a second subset of layers of the neural network by concatenating the preliminary classification with the output of a layer of the first subset of layers that precedes the final layer of the first subset of layers;

within the second subset of layers of the neural network, performing a second series of convolution operations;

in a final layer of the second subset of layers, determining a final classification comprising a plurality of final classification estimates, each final classification estimate corresponding with a time segment of the ECG signal.

At least some of the convolution operations in the first subset of layers may be dilated convolution operations.

Successive dilated convolution operations in the first subset of layers may have increasing dilation factor.

The dilation factor of the successive dilated convolution operations in the first subset of layers may increase by factor of 2 in each successive layer.

At least some of the convolution operations in the second subset of layers may be dilated convolution operations.

Successive dilated convolution operations in the second subset of layers may have increasing dilation factor The dilation factor of the successive dilated convolution operations in the second subset of layers may increase by factor of 2 in each successive layer.

The time segment corresponding with each final classification estimate may be less than 1 second, or less than 0.5 second.

The final classification estimates may include an estimate as to the probability of each time segment comprising atrial fibrillation.

The final classification estimates may include an estimate as to the probability of each time segment comprising at least one of: "noise", a "normal" ECG and "other".

According to a second aspect, there is provided a method of training a neural network, comprising:

using a neural network to determine a preliminary classification and a final classification for each of a plurality of time periods of an ECG signal with an initial set of convolution filter values;

determining a penalty function responsive to both the preliminary classification and the final classification, using training classification data for each time period; and adjusting the convolution filter values to minimise the penalty function.

The training classification may be determined by replicating a single classification for the whole ECG signal in each of the time periods.

According to a third aspect, there is provided a non-transitory machine readable medium comprising instructions for causing a computer to perform the method according to the first or second aspect.

According to a fourth aspect, there is provided a system for improving cardiovascular health, comprising:

a computer comprising:

a data reception module for receiving ECG data obtained from a test subject;

a neural network for determining a final classification comprising a plurality of final classification estimates, each final classification estimate corresponding with a time segment of the ECG signal, wherein the neural network comprises:

a first subset of layers performing a first series of convolution operations, and determining a preliminary classification comprising a plurality of preliminary classification estimates, each preliminary classification estimate corresponding with a time segment of the ECG signal; and a second subset of layers that receive the preliminary classification and the output of a layer of the first subset of layers that precedes the final layer of the first subset of layer, the final layer of the second subset of layers determining a final classification comprising a plurality of final classification estimates, each final classification estimate corresponding with a time segment of the ECG signal; and a reporting module for reporting the final classification estimate to a subject and/or cardiologist.

The computer may be a server, and the data reception module may receive the ECG data via a network.

The computer may be a mobile device, and the data reception module may comprise a wireless receiver.

The reporting module may be accessible using a web based interface, and may be configured to overlay the final classification estimate on the ECG signal to draw attention to regions of the ECG with a specific classification.

The specific classification may comprise atrial fibrillation.

The system may further comprise a wearable ECG device for obtaining the ECG signals from the subject.

The system may further comprise a mobile device configured to wirelessly receive the ECG signals from the wearable ECG device, and to transmit the ECG signals to the computer.

Each of the features of each aspect (including optional features) may be combined with those of any other aspect.

BRIEF DESCRIPTION OF THE DRAWINGS

Embodiments of the invention will be described, purely by way of example, with reference to the accompanying drawings, in which.

DETAILED DESCRIPTION OF THE PREFERRED EMBODIMENTS

Figure 1:
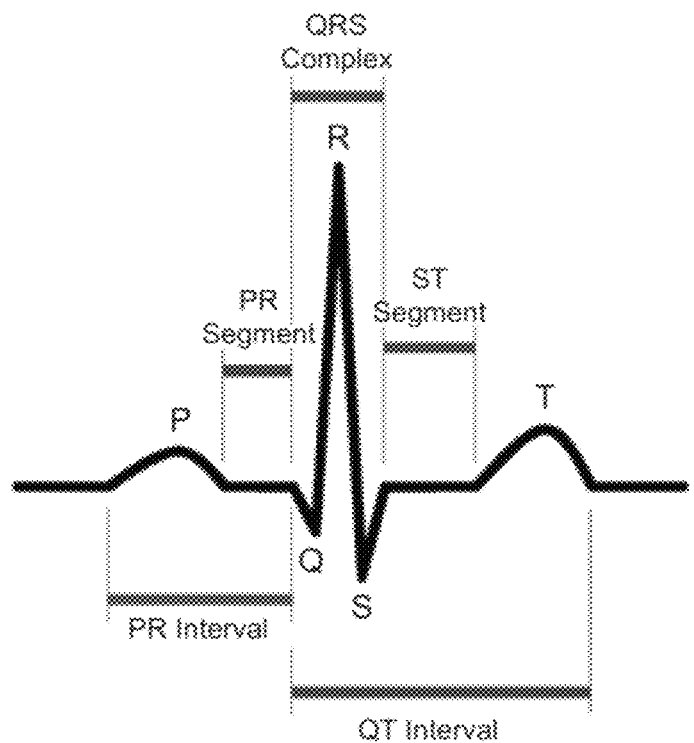
FIG. 1 is a graph of a basic electrocardiograph (ECG) signal.
Figure 2:
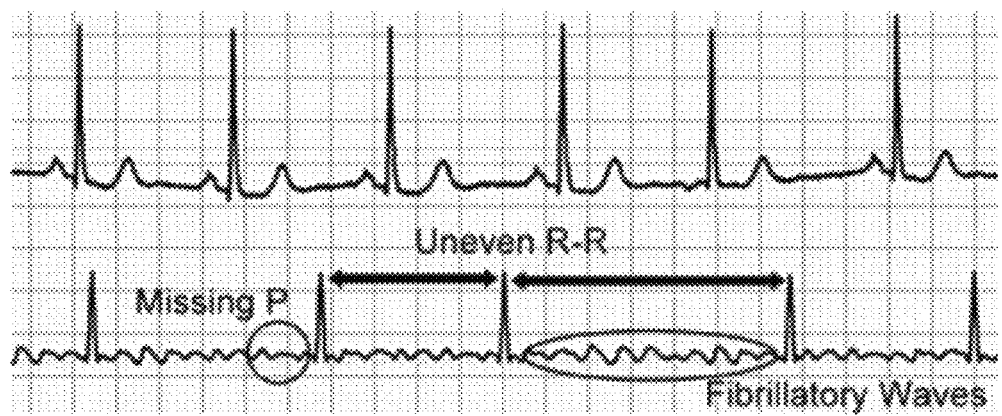
FIG. 2 is a series of ECG signals which may be used for the detection of AF by doctors in clinics.
Figure 3:
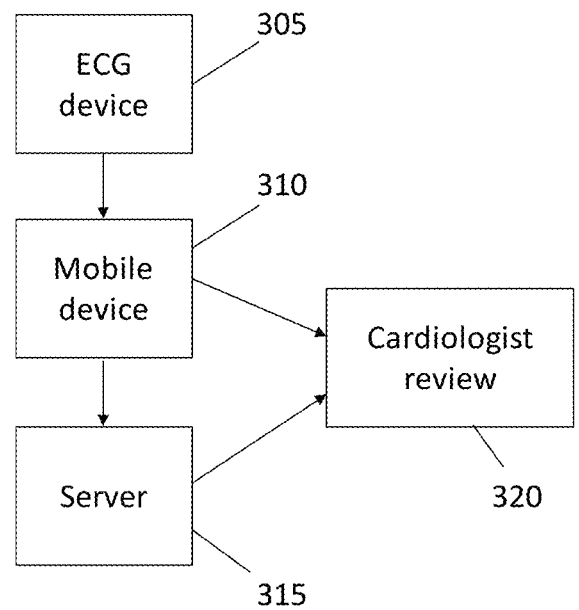
FIG. 3 is an exemplary overall architecture according to an embodiment.

FIG. 3 illustrates an exemplary overall system architecture according to one embodiment of the present invention.

An ECG device 305 is provided, which comprises at least one electrode and an associated readout circuit for obtaining electrocardiogram signals from the subject. The ECG device may further comprise an analogue to digital converter for converting the ECG signal and performing any necessary processing to produce an ECG data. A microprocessor or microcontroller may be provided, configured to perform some processing on the electrocardiogram data (e.g. normalisation, filtering etc). The ECG device may further comprise a transmitter for wirelessly communicating raw or processed ECG data, for example over a low energy Bluetooth channel, or any other wireless communication channel.

The ECG device 305 may be wearable and may comprise a chest strap for holding the at least one electrode in contact with the subject in spaced apart configuration. The ECG device 305 may comprise a single electrode, or multiple electrodes.

The mobile device 310 is configured to receive the ECG data from the ECG device 305 via a data reception module (e.g. a wireless communication module). The mobile device 310 may be configured to buffer and upload the ECG data to the server 315 and/or may be configured to perform some analysis of the ECG. In some embodiments, the mobile device 310 may be configured to check for emergencies like cardiac arrest. The mobile device 310 may be responsive to the analysis, for example to send an alert or message to the cardiologist in the case of a significant abnormality. The mobile device 310 comprises a transmitter to communicate data to the server (e.g. via a mobile data communication network, such as 3G, 4G etc).

In some embodiments, the mobile device 310 is configured to perform a pre-analysis, and the server 315 is configured to run a more developed analysis on the ECG data. In some embodiments, the mobile device 310 may be configured to perform a full analysis of the ECG data locally using a neural network, and may comprise a reporting module for transmitting a report including the analysis to the server, or to a user (e.g. via a display of the mobile device).

The server comprises a data reception module for receiving data via a network and a reporting module for reporting the final classification estimate to the subject and/or cardiologist. The neural network (whether it is implemented on the mobile device or the server) may provide a preliminary classification of the ECG data. The reporting module may provide a report in which regions of interest in the ECG data are highlighted to facilitate straightforward review by the cardiologist 320. This may greatly reduce the workload on the cardiologist 320, and render feasible monitoring of subject ECGs over long periods (e.g. continuously or nearly so).

Figure 4:
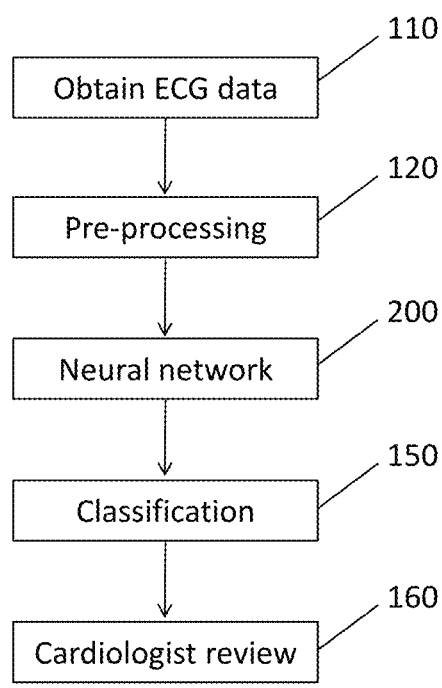
FIG. 4 is an overall methodology for detecting abnormalities in ECG signals according to one embodiment.

Referring to FIG. 4, an overview of a process for identifying abnormalities in ECG data is shown.

At 110 ECG data is obtained, for example using the ECG device 305 described with reference to FIG. 3, or from either the mobile device 310 or the server 315.

At 120 the ECG data is pre-processed. This may comprise at least one of filtering, normalising and re-sampling the data to a specific data rate. In an embodiment, the pre-processing step may comprise re-sampling ECG data. The re-sampling may be at a rate of at least 60 Hz, and preferably at least 100 Hz (e.g. 120 Hz). In some embodiments the pre-processing step may be omitted, and raw ECG data provided to the neural network.

At 200 a neural network is used to classify the ECG data. The neural network may be a convolutional neural network (CNN), and is configured to provide a classification output 150. The classification 150 may be dense, for example having a rate of at least 2 Hz, preferably at least 5 Hz (for example 7.5 Hz).

The classification output from the neural network may comprises a set of probabilities corresponding with each of a plurality of classifications for each time period of the input ECG signal. For example, the neural network may use classifications of "AF" and "not-AF", and the classification output may provide an estimate of the probability for each 0.2 s period of the input signal (i.e. at 5 Hz) being "AF" and "not-AF". Since these example classifications are mutually exclusive, the sum of their probabilities will be equal to 1, but it will be appreciated that this will not necessarily be the case (depending on what classifications are sought from the neural network). Other classification types may be used, and the classification frequency may differ from 5 Hz (which is merely by way of example). The actual classification frequency will depend on the architecture of the neural network, as be apparent from the discussion below.

In some embodiments the neural network may be implemented on a server (e.g. in the cloud, and/or remote from the user), for example by providing using GPU processing, or on a specialised neural processing unit (e.g. Intel Nervana, Google Tensor processing unit, Apple Neural Engine, Cadence Tensilica or similar). The neural network may be hosted by a cloud computing service such as Amazon Machine Learning services, Azure Machine Learning, Google Cloud AI or similar.

A server based neural network (or cloud service) may be able to rapidly and efficiently process data from a large amount of different users, and provide a platform that can be accessed by a cardiologist to review the information. In other embodiments the neural network may be implemented locally (for example on a mobile device). This may mean that patient identifiable data is be kept local to the patient's own device.

The results may be made available for review by a cardiologist, for example via a web accessible platform. The platform may provide ECG data to the cardiologist with regions of particular interest highlighted, based on the classification 150 from the neural network. For example, regions classified as "AF" with a probability of greater than a predetermined threshold (e.g. 0.8) may be flagged or highlighted for further review by a cardiologist. A duration based threshold may also be used in determining regions of interest (e.g. AF with a probability of >0.8, over a time period of at least 2 seconds).

Figure 5:
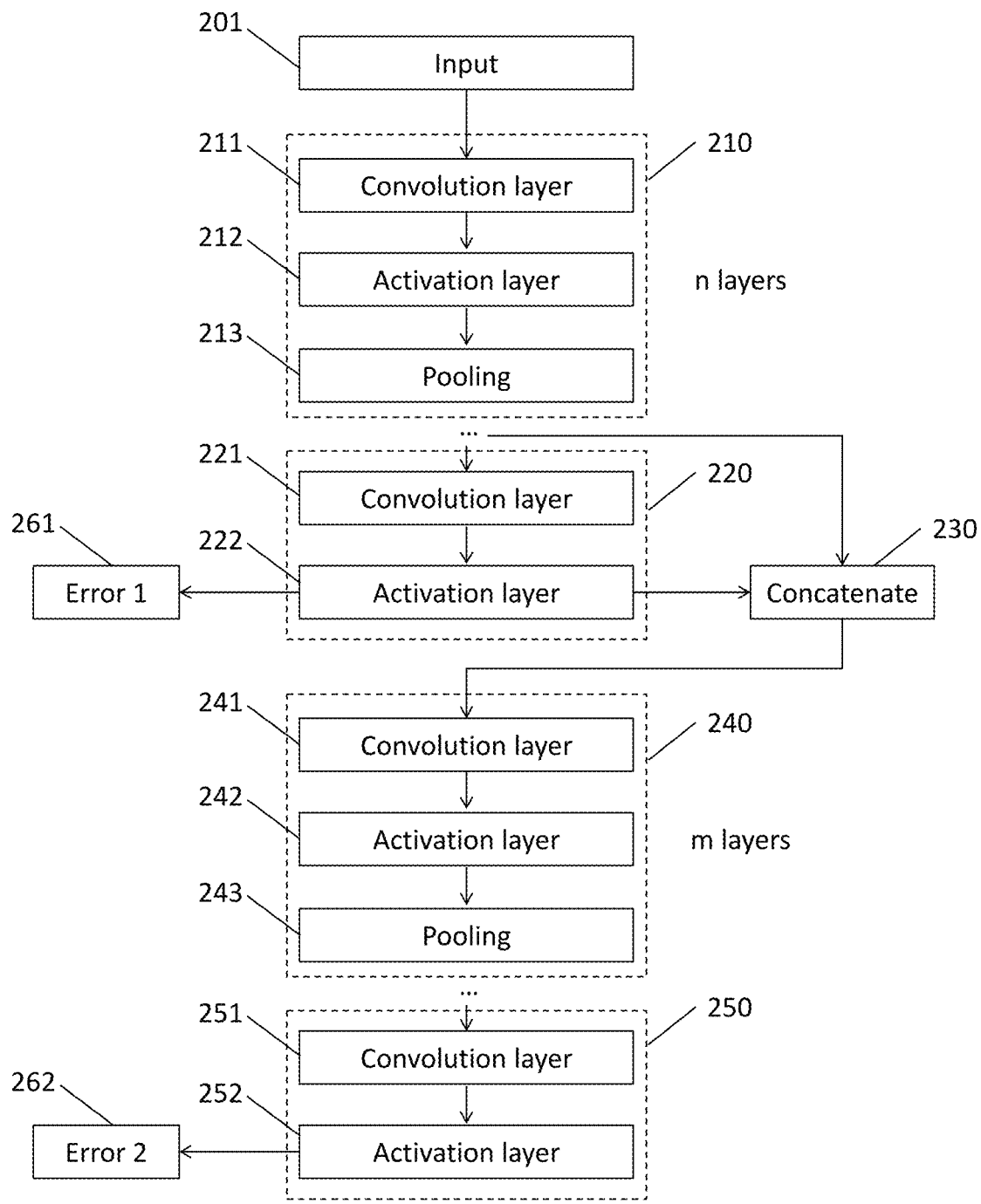
FIG. 5 is a schematic diagram of a neural network for use in an embodiment.

FIG. 5 illustrates an example neural network in schematic form for classifying ECG data to identify abnormalities (such as AF). The neural network comprises an input layer 201 followed by a first subset of layers 210, 220 which produce preliminary estimate classification estimates. These preliminary classification estimates are concatenated with an output of a preceding layer and provided to a second subset of layers 240, 250. The second subset of layers provide the (final) classification estimates 150 referred to in FIG. 4.

The first subset of layers comprises n superlayers 210 and a pre-prediction superlayer 220. Each superlayer 210 comprises a convolution layer 211, activation layer 212 and pooling layer 213. In some embodiments, the pooling layer may be omitted in one or more superlayers.

Each convolution layer 211 applies one or more convolution filters (or kernels) by stepping the filter over the data provided to that layer (the steps having a predetermined stride distance). The output from each convolution layer 211 comprises the data produced from the convolution of the input data with each filter.

At least one of the convolution layers 211 may apply a dilated convolution. A dilated convolution spaces out the data to which the convolution filter is applied, and can be thought of as equivalent to using a sparse filter in which the filter parameters are padded with zeros. Dilated convolution layers may increase the receptive field of convolution operations without the need for a filter/kernel with high dimensions. A compact filter/kernel can instead be used, and successive dilation used to increase the receptive field of subsequent neurons in the later convolution layers. In some embodiments, the dilation factors in each successive convolution layer 211 in the first subset of layers follow a geometric progression (e.g. a convolution factor in super-layer i of $2^i$).

Figure 6:
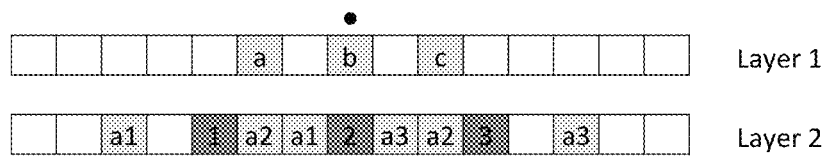
FIG. 6 illustrates the effect of dilated convolutions in expanding the receptive field of neurons.

FIG. 6 illustrates this concept. The input data to layer 1 is a vector, represented by a line of boxes. The convolution filter here is 1×3×1, with weights a, b and c, and a dilation factor of 2. The filter is centred on the data indicated by •. In the second layer, a further convolution filter is applied, also with dimension 1×3×1, with weights 1, 2 and 3. The receptive field of the neuron in layer 2 at • comprises the data in layer 1 that is used to determine this neuron, which is indicated by a1, a2 and a3, respectively indicating positions. Dilating the convolution operations therefore provides a computationally efficient method for enabling a neural network to recognise features with large spatial extent (which may be particularly applicable to ECG processing), and/or for producing a dense classification (i.e. with a specific frequency, rather than a single classification for the whole signal).

Subsequent to the convolution layer 211, an activation layer 212 is provided, which maps the output of the convolution layer 211 to a different range of values. Typically, the activation function used in each of layers 210 will be a rectified linear activation function (ReLU), but other activation functions may also be used.

Following each activation layer 212 (e.g. ReLU), a pooling layer 213 may be provided to reduce the spatial dimension of the data before the next layer. Typically, the pooling function used may be a max pooling with a stride greater than 1, but other pooling approaches may also be used. The output from the pooling layer is provided to the subsequent superlayer 210, 220.

The sequence of n superlayers 210 are followed by the pre-prediction superlayer 220, which comprises a convolution layer 221 and an activation layer 222. The output from the activation layer 222 is a preliminary estimate for the classifications. An error 261 can be determined from this preliminary prediction part of the neural network, which may be used as part of a penalty function in training the network. The error 261 may be determined in the form of a cross entropy loss. The use of a pre-prediction error in training the network may make training the network faster and more reliable.

The output from the pre-prediction activation layer 222 is concatenated 230 with the output of the superlayer 210 preceding the pre-prediction superlayer 220, so as to provide data, comprising pre-prediction classification estimates and a set of features for further refining the classification estimates, to the subsequent layers of the network.

The output of the concatenation 230 is provided to a second subset of layers 240, 250, which comprises m superlayers 240 and a final prediction superlayer 250. Each superlayer 240 comprises a convolution layer 241, activation layer 242 and pooling layer 243.

Each convolution layer 241 applies one or more convolution filters (or kernels) by stepping the filter over the data input to that layer (the steps having a predetermined stride distance). The output from each convolution layer 241 comprises the data produced from the convolution of the input data with each filter. The convolution layers in the second subset may also comprise dilated convolution layers, for example with successively increasing convolution factor, as described with reference to the first subset of layers (re-setting to the same initial value of dilation factor, e.g. 2).

Subsequent to the convolution layer 241, an activation layer is provided, which maps the output of the convolution layer 241 to a different range of values. Typically, the activation function used in each of layers 240 will be a rectified linear activation function (ReLU), but other activation functions may also be used.

Following each activation layer (e.g. ReLU), a pooling layer 243 may be provided to reduce the spatial dimension of the data before the next layer. Typically, the pooling function used may be a max pooling with a stride greater than 1, but other pooling approaches may also be used. The output from the pooling layer 243 is provided to the subsequent superlayer 240, 250.

The sequence of m superlayers 240 are followed by the final prediction superlayer 250, which comprises a convolution layer 251 and an activation layer 252. The output from the activation layer 252 may be a final estimate for the classification probabilities. An error 262 is determined from this pre-prediction part of the neural network, which is used as part of a penalty function in training the network. The error 262 may be determined in the form of a cross entropy loss. A final prediction for the class of each segment may be found by using an Argmax function to identify the classification with the highest probability. A class for the whole ECG may be identified as the mode class over all segments.

The combination of a pre-predicting architecture and successive dilations may enable a relatively compact network, with a relatively small number of neurons (i.e. computationally efficient, both to train and run), that is still able incorporate large amounts of context in its classification.

Figure 7:
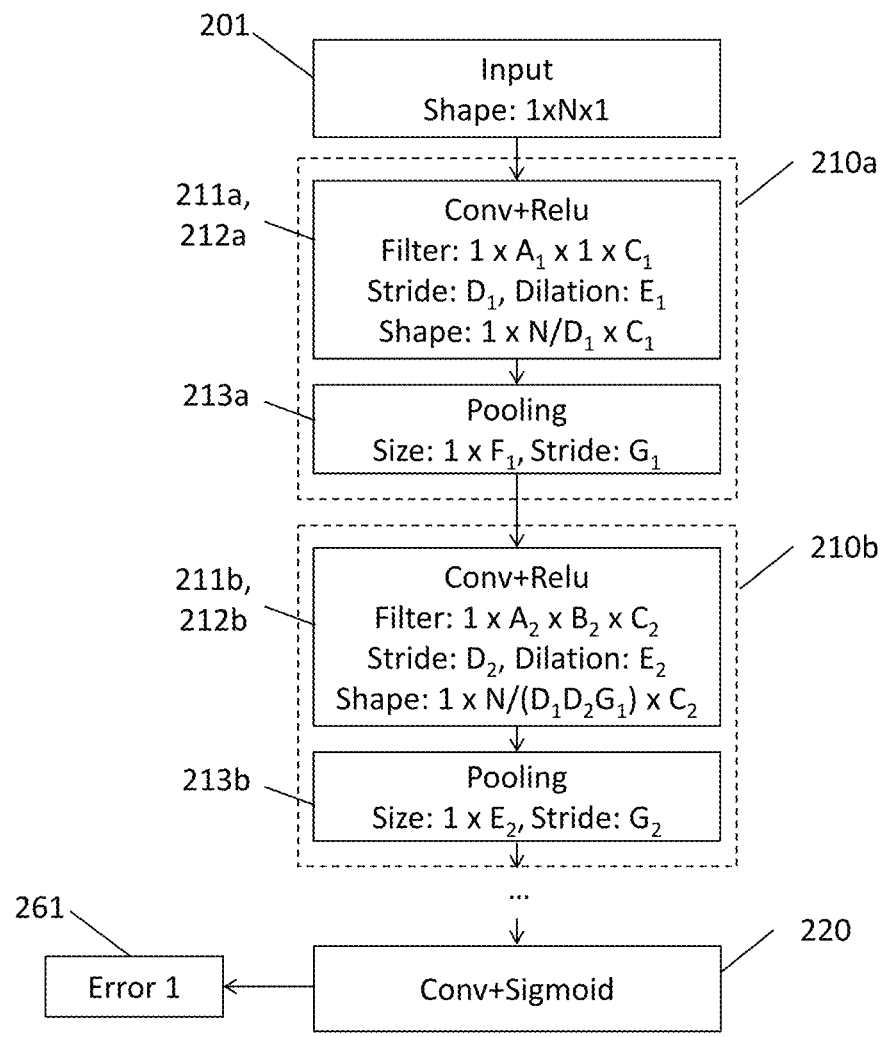
FIG. 7 is a schematic diagram of a first subset of layers of a neural network for use in an embodiment.

FIG. 7 illustrates an example architecture for the first subset of layers in more detail. The input layer 201 comprises an input vector of ECG data, with dimension 1×N×1, with the second dimension N being the number of samples (i.e. corresponding with time). In some embodiments the (first) dimension of the input data may be higher, for example in the case of input data comprising having a multiple channels (e.g. each corresponding with raw data obtained from each of a plurality of electrodes).

The input data is provided to first superlayer 210a, which comprises a convolution layer (cony) 211a, and ReLU layer 212a. The first cony layer 210a may apply $C_1$ filters, each having a kernel of dimension 1×$A_1$×1, with a dilation factor $E_1$ and a stride of $D_1$. The shape of the output from the cony and ReLU 211a, 212a is of dimension 1×N/$D_1$×$C_1$ (the length of the vector is decreased in proportion to the stride, and the third dimension (which can be thought as as rows) increased in proportion to the number of filters applied by the cony layer 211a, since there is an output vector per filter). The number of filters $C_1$ in the first cony layer 210a may be at least 8, and may be in the range 8 to 64, for example 16 or 32. The stride of the cony 211a may be 1, so that the neural network can discriminate features with maximum resolution.

The subsequent pooling layer has a size 1×$F_1$ and a stride $G_1$>1, so that the second spatial dimension following the pooling is reduced by a factor of $G_1$. The next superlayer 210b therefore receives data with extent 1×N/($D_1G_1$)×$C_1$.

The second superlayer 210b comprises $C_2$ filters, each with extent $1 \times A_2 \times B_2$. Preferably, $B_2 = C_1$ (or more generally for i≥2, $B_i = C_{i-1}$), so that each cony filter is stepped over all the data from the previous layer in only one direction. The number of filters $C_2$ in the second superlayer 210b is preferably in the range 32 to 256, for example 128. The output from the second cony and ReLU 211b, 212b is of dimension $1 \times N/(D_1 D_2 G_1) \times C_2$. The stride of the second cony layer 211b (and successive layers) is preferably 1, for the same reasons as for the first layer, but this is not essential (for example, a higher stride may be appropriate for ECGs data with high sampling frequency).

The temporal resolution of the output of each successive layer is reduced by the product of the stride distances of the preceding layers, and may successively decrease, In the case of a n=4, with four superlayers 210 preceding the final cony layer 220 in the first subset, and each superlayer 210 having a cony stride of 1 and a pooling layer stride of 2, the temporal resolution of the classification will be a factor of $2^4$ less than the sampling rate of the ECG (so a 120 Hz sampling rate in the ECG would lead to a classification rate of 7.5 Hz: a preliminary classification estimate for each 133 ms period of the ECG).

The preliminary classification is produced using a filter for each classification type (e.g. "AF" "Normal" etc), followed by a sigmoid activation layer, which maps the output of each filter onto a classification estimate that sums to 1 across all the possible classifications (producing a probability estimating whether that particular period of the ECG data is within each classification).

The second subset of layers may be configured similarly to the first subset, except that instead of receiving input ECG data, the second subset receives a concatenation of the output from the n superlayers 210 preceding the preliminary classification superlayer 220. The cony layer in 220 preferably has a stride of 1 so that the data has the same length (second dimension) so that it can easily be concatenated in the form of extra rows of data.

A neural network following the architecture described in FIGS. 6 and 7 was implemented, capable of receiving resampled raw ECG data and producing dense classification and reliable identification of AF. The neural network was trained using the AF Challenge 2017 dataset, using the RMSprop optimizer until convergence. The dataset used for training included only a single ground truth label for each ECG recording (of up to 60 seconds). The training requires a true classification for each time segment of the ECG signal, and so the single signal was replicated across all segments for training purposes, and the training loss computed as the mean cross-entropy loss over all segments. The resulting neural network was capable of outputting a reliable dense classification probability, which will enable a cardiologist to immediately focus their attention on the most relevant portion of the ECG signal, thereby saving time and improving patient outcomes. Initial embodiments of example classification networks have a true positive rate of 89% (tested on a reserved set of the dataset used to source training data), with a false positive (for AF) of approximately 3%.

Figure 8:
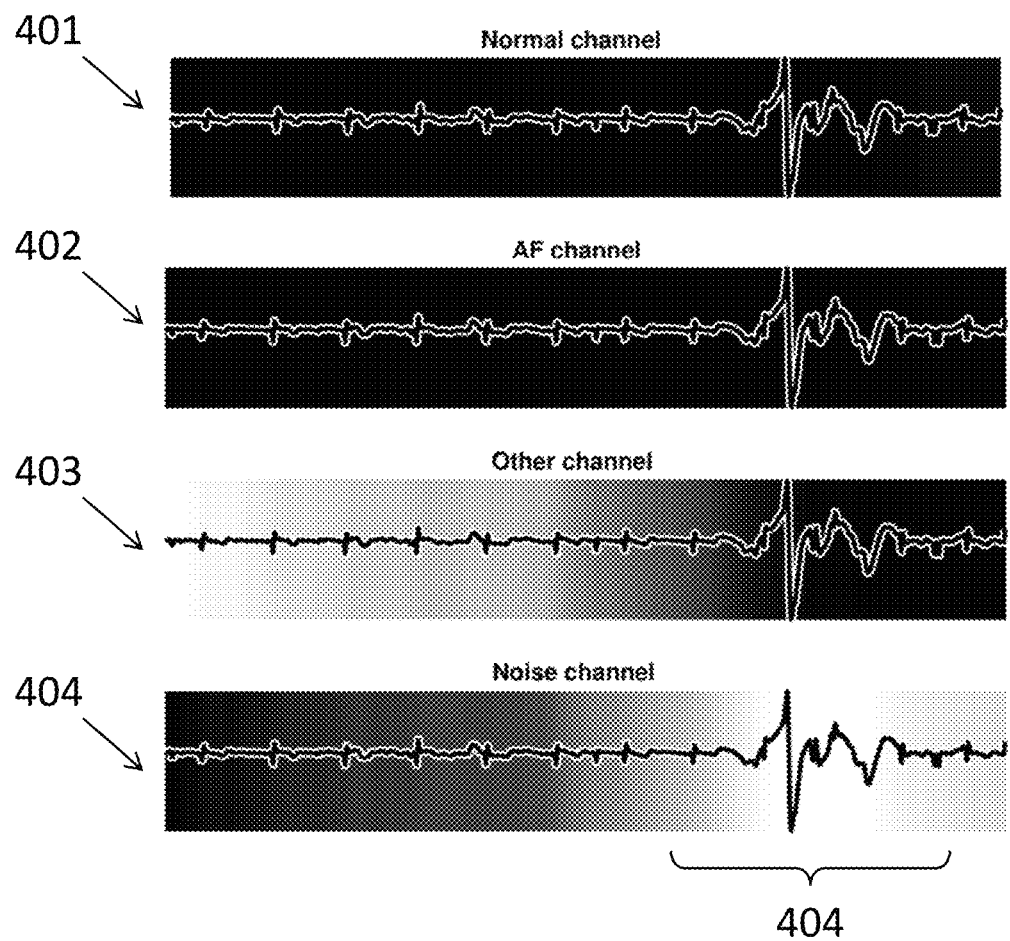
FIG. 8 is a set of graphs showing example final classification estimates obtained according to an embodiment.

FIG. 8 illustrates classifications for ECG data obtained according to an embodiment, showing, for a particular region of ECG data, the classification estimates 401-404 for each category. The categories are respectively 401 "Normal", 402 "AF", 403 "Other" and 404 "Noise" (e.g. resulting from subject movement). White corresponds with a high probability, and black to a low probability. The neural network accurately identifies a period of noise 404, and also accurately classifies the abnormal signals preceding this as "Other" i.e. not "Normal", "AF" or "Noise".

Figure 9:
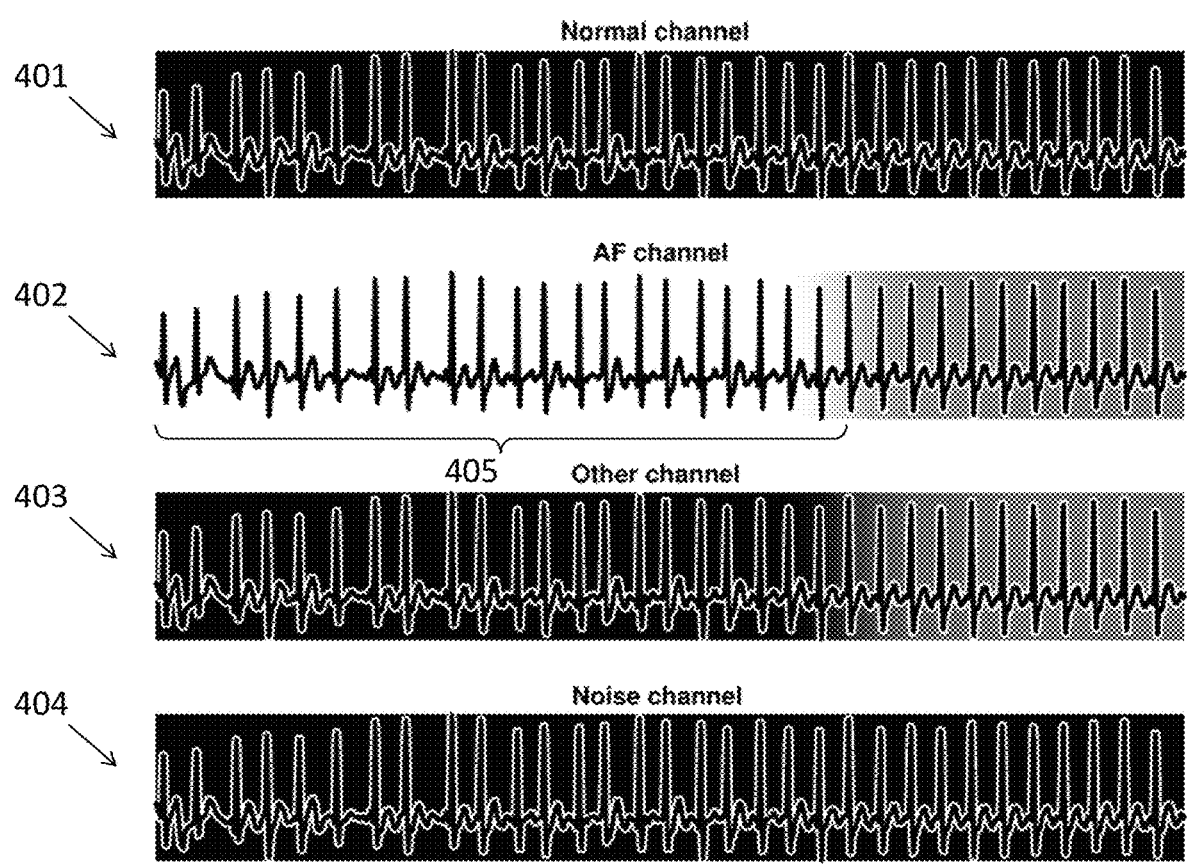
FIG. 9 is a further set of graphs showing example final classification estimates obtained according to an embodiment.

FIG. 9 illustrates a similar classification, in which a period 405 is identified as having a high probability of being atrial fibrillation. The neural network can be used to highlight this sort of region in an ECG for review by a cardiologist. Alternatively or additionally, a system according to the invention can log the accumulation of high probability AF periods within a specific time frame (e.g. a week), and alert the subject or their cardiologist if the accumulation exceeds a predetermined threshold (which may be lower than a clinical threshold for AF). The early identification of pre-clinical AF may enable the subject to take early measures to improve their health.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Although a number of examples have been described, these are not intended to limit the scope of the invention, which is to be determined with reference to the accompanying claims.

The invention claimed is:

1. A method of detecting abnormalities in ECG signals, comprising:
    providing an ECG signal to a neural network;
    within a first subset of layers of the neural network, performing a first series of convolution operations;
    in a final layer of the first subset of layers, determining a preliminary classification comprising a plurality of preliminary classification estimates, each preliminary classification estimate corresponding with a time segment of the ECG signal;
    determining input data for a second subset of layers of the neural network by concatenating the preliminary classification with an output of a layer of the first subset of layers that precedes the final layer of the first subset of layers;
    within the second subset of layers of the neural network, performing a second series of convolution operations; and
    in a final layer of the second subset of layers, determining a final classification comprising a plurality of final classification estimates, each final classification estimate corresponding with a time segment of the ECG signal;
    wherein at least some of the convolution operations in at least one of the first and the second subset of layers are dilated convolution operations.

2. The method of claim 1, wherein at least some of the convolution operations in the first subset of layers are dilated convolution operations.

3. The method of claim 2, wherein successive dilated convolution operations in the first subset of layers have an increasing dilation factor.

4. The method of claim 3, wherein the dilation factor of the successive dilated convolution operations in the first subset of layers increases by a factor of 2 in each successive layer.

5. The method of claim 1, wherein at least some of the convolution operations in the second subset of layers are dilated convolution operations.

6. The method of claim 5, wherein successive dilated convolution operations in the second subset of layers have an increasing dilation factor.

7. The method of claim 6, wherein the dilation factor of the successive dilated convolution operations in the second subset of layers increases by a factor of 2 in each successive layer.

8. The method of claim 1, wherein the time segment corresponding with each final classification estimate is less than 1 second, or less than 0.5 second.

9. The method of claim 1, wherein the final classification estimates include an estimate as to the probability of each time segment comprising atrial fibrillation.

10. The method of claim 9, wherein the final classification estimates include an estimate as to the probability of each time segment comprising at least one of: a noise, a normal ECG and other.

11. The method of claim 1, further comprising training the neural network, comprising:
   determining a preliminary classification and a final classification for each of a plurality of time periods of an ECG signal with an initial set of a convolution filter values for the neural network;
   determining a penalty function responsive to both the preliminary classification and the final classification, using training classification data for each time period; and
   adjusting the convolution filter values to minimise the penalty function.

12. The method of claim 11, wherein the training classification is determined by replicating a single classification for the whole ECG signal in each of the time periods.

13. A non-transitory machine readable medium comprising instructions for causing a computer to perform the method in accordance with claim 1.

14. A system for improving cardiovascular health, comprising:
   a computer comprising:
      a data reception module for receiving ECG data obtained from a test subject; and
      a neural network for determining a final classification comprising a plurality of final classification estimates, each final classification estimate corresponding with a time segment of the ECG signal, wherein the neural network comprises:
         (i) a first subset of layers performing a first series of convolution operations, and determining a preliminary classification comprising a plurality of preliminary classification estimates, each preliminary classification estimate corresponding with a time segment of the ECG signal; and
         (ii) a second subset of layers that receive the preliminary classification and an output of a layer of the first subset of layers that precedes a final layer of the first subset of layer, a final layer of the second subset of layers determining a final classification comprising a plurality of final classification estimates, each final classification estimate corresponding with a time segment of the ECG signal,
   wherein at least some of the convolution operations in at least one of the first and the second subset of layers are dilated convolution operations;
   the computer further comprising:
      a reporting module for reporting the final classification estimate to a subject and/or cardiologist.

15. The system of claim 14, wherein the computer is a server, and the data reception module receives the ECG data via a network.

16. The system of claim 14, wherein the computer is a mobile device, and the data reception module comprises a wireless receiver.

17. The system of claim 14, wherein the reporting module is accessible using a web based interface, and is configured to overlay the final classification estimate on the ECG signal to draw attention to regions of the ECG with a specific classification.

18. The system of claim 17, wherein the specific classification comprises atrial fibrillation.

19. The system of claim 14, further comprising a wearable ECG device for obtaining the ECG signals from the subject.

20. The system of claim 19, further comprising a mobile device configured to wirelessly receive the ECG signals from the wearable ECG device, and to transmit the ECG signals to the computer.

* * * * *